(12) United States Patent
Courtney et al.

(10) Patent No.: US 10,060,871 B2
(45) Date of Patent: Aug. 28, 2018

(54) TEST APPARATUS AND METHOD FOR TESTING AN ELECTRICAL PROPERTY OF A FLUID

(71) Applicant: Megger Instruments Ltd, Dover (GB)

(72) Inventors: Anthony Courtney, Dover (GB); Stanislaw Zurek, Dover (GB); Simon Haynes, Dover (GB)

(73) Assignee: MEGGER INSTRUMENTS LTD, Kent, Dover (GB)

( * ) Notice: Subject to any disclaimer, the term of this patent is extended or adjusted under 35 U.S.C. 154(b) by 0 days.

(21) Appl. No.: 15/849,472

(22) Filed: Dec. 20, 2017

(65) Prior Publication Data

US 2018/0113089 A1    Apr. 26, 2018

Related U.S. Application Data

(63) Continuation of application No. PCT/GB2016/051851, filed on Jun. 21, 2016.

(30) Foreign Application Priority Data

Jun. 23, 2015 (GB) .................................. 1511041.4

(51) Int. Cl.
*G01R 27/08* (2006.01)
*G01N 27/07* (2006.01)
(Continued)

(52) U.S. Cl.
CPC ............ *G01N 27/07* (2013.01); *G01N 27/14* (2013.01); *G01N 27/226* (2013.01); *G01N 33/28* (2013.01)

(58) Field of Classification Search
CPC .... G01N 27/07; G01N 27/226; G01N 27/121; H01T 13/60; H01T 21/02; H01T 23/00;
(Continued)

(56) References Cited

U.S. PATENT DOCUMENTS

| 3,471,628 A * | 10/1969 | Harmon ................. | H02G 15/06 |
| | | | 174/12 BH |
| 3,924,445 A * | 12/1975 | Konomi ................... | G01F 1/36 |
| | | | 73/1.26 |
| 2016/0003756 A1* | 1/2016 | Suzuki ................... | G01N 27/06 |
| | | | 210/767 |

FOREIGN PATENT DOCUMENTS

| AU | 6445380 | 5/1981 |
| CN | 201075092 | 6/2008 |
| | (Continued) | |

OTHER PUBLICATIONS

L.N. Bramley "An improved cell for AC and DC testing of insulating oils", Journal of the Institution of Electrical Engineers, Apr. 1940.

(Continued)

*Primary Examiner* — Vinh Nguyen
(74) *Attorney, Agent, or Firm* — EIP US LLP

(57) ABSTRACT

Test apparatus is provided for testing an electrical property of a fluid. The apparatus comprises an electrically conductive container (1) forming an outer electrode of a test cell for containing the fluid, an inner electrode (2) of the test cell, an inductive heating assembly (3) and a cooling means. The inner electrode (2) of the test cell is arranged, when mounted relative to the electrically conductive container (1), to project into, and remain electrically isolated from, the electrically conductive container (1). The inductive heating assembly (3) comprises an inductive heating coil (4), which surrounds the electrically conductive container (1), for heating the electrically conductive container (1) and the inner electrode (2). The cooling means comprises an air channel (9) to allow passage of air across a surface of the electrically conductive container (1), for cooling of the electrically conductive container (1).

20 Claims, 7 Drawing Sheets

(51) Int. Cl.
  *G01N 27/14* (2006.01)
  *G01N 27/22* (2006.01)
  *G01N 33/28* (2006.01)

(58) Field of Classification Search
  CPC ...... G01R 15/04; G01R 27/14; G01R 31/027;
      G01R 31/12; G01R 31/16; H01G 4/224;
      H01B 3/20; H01F 27/14; H01F 27/402;
      H01F 27/125; G01K 1/08; G01K 1/14;
      G01K 7/00
  See application file for complete search history.

(56) References Cited

FOREIGN PATENT DOCUMENTS

| GB | 1218200 | 1/1971 |
|----|---------|--------|
| JP | S63243743 | 10/1988 |
| JP | 2001153830 | 6/2001 |

OTHER PUBLICATIONS

R.G. Heydon: "A versatile three-terminal test cell for dielectric measurements on insulating liquids", IEEE Transaction on Electrical Insulation, Aug. 1989.
ELTEL: "Scroll Jan. 2011 Oil test cell & oil test cell heater Oil Test Cell", Jan. 1, 2011.
International Search Report dated Oct. 7, 2016 for PCT Application No. PCT/GB2016/051851.
Written Opinion dated Oct. 7, 2016 for PCT Application No. PCT/GB2016/051851.
Search Report dated Dec. 1, 2015 for GB Application No. GB1511041.4.

* cited by examiner

TEST APPARATUS AND METHOD FOR TESTING AN ELECTRICAL PROPERTY OF A FLUID

CROSS-REFERENCE TO RELATED APPLICATIONS

This application is a continuation of International Application No. PCT/GB2016/051851, filed Jun. 21, 2016, which claims priority to GB Application No. 1511041.4, filed Jun. 23, 2015, under 35 U.S.C. § 119(a). Each of the above-referenced patent applications is incorporated by reference in its entirety.

BACKGROUND OF THE INVENTION

Field of the Invention

The present invention relates generally to methods and apparatus for testing an electrical property of a fluid, and more specifically, but not exclusively, to test apparatus comprising a test cell for measuring the resistivity, tan delta dissipation factor, and/or permittivity of an insulating oil.

Description of the Related Technology

Electrical properties of a fluid may need to be tested, for example to evaluate whether the fluid conforms to relevant standards. For example, the resistivity and/or tan delta dissipation factor of insulating oil used in electrical transformers may need to be tested periodically, over a range of temperatures, to ensure that the resistivity is within specified limits. The resistivity and/or dissipation factor of the oil may degrade with age and by contamination, and, if the resistivity falls below specified limits, this may present a safety hazard. Test equipment is available, in which a sample of the fluid to be tested is introduced into a test cell having an electrically conductive outer container into which an electrically conductive inner electrode projects. The outer container and inner electrode are typically milled from metal and made to close tolerances, and are constructed in such a way that a gap of specified dimensions is maintained between them, in which the fluid is contained. In this way, the electrical properties of the fluid may be determined by measuring a voltage and/or current between the outer container and the inner electrode, given that the thickness of the fluid layer and volume of fluid are known.

The electrical properties of the fluid may be measured at a number of specified temperatures by heating the test cell, typically by inductive heating using an inductive heating coil arranged to surround the test cell. Typically, the heat capacity of the test cell is arranged to be sufficiently high to reduce temperature fluctuations of the cell, so that the cell is maintained at a substantially constant temperature during a measurement. However, as a result of the high heat capacity of the cell, the cell may remain hot after a test for an extended period, which may make safe handling of the cell difficult, and which may extend the time needed to perform temperature test cycles.

It is an object of the invention to address at least some of the limitations of the prior art systems.

SUMMARY

In accordance with a first aspect of the present invention, there is provided test apparatus for testing an electrical property of a fluid, the apparatus comprising:

an electrically conductive container for containing the fluid, the electrically conductive container forming an outer electrode of a test cell;

an inner electrode of the test cell arranged when mounted relative to the electrically conductive container to project into, and to remain electrically isolated from, the electrically conductive container;

an inductive heating assembly comprising an inductive heating coil, which surrounds the electrically conductive container for heating the electrically conductive container and the inner electrode; and cooling means comprising an air channel to allow the passage of air across a surface of the electrically conductive container, for cooling the electrically conductive container.

An advantage of providing cooling means comprising an air channel to allow passage of air across a surface of the electrically conductive container is that the test cell may be cooled by the passage of air through the air channel, thereby to reduce the time taken for the test cell to cool sufficiently for safe handling after a test.

In an embodiment of the invention, the air channel is provided between the inductive heating assembly and the electrically conductive container. This allows efficient cooling of the electrically conductive container.

In an embodiment of the invention, the air channel is provided between the inductive heating coil and the electrically conductive container.

In an embodiment of the invention, the inductive heating assembly and the electrically conductive container are arranged such that the air channel allows the passage of air across at least part of the outer surface of the electrically conductive container. This allows efficient cooling of the electrically conductive container.

In an embodiment of the invention, the cooling means comprises a fan assembly arranged to cause air to flow through the air channel.

This allows a flow rate of air that is sufficient to produce a desired cooling effect to be maintained through a narrow air channel.

In an embodiment of the invention, the air channel comprises an air gap of at least 1 mm between the inductive heating assembly and the electrically conductive container for most of the outer surface of the electrically conductive container.

This allows a flow rate of air to be maintained to produce a desired cooling effect.

In an embodiment of the invention, the air gap is in the range 2 mm to 4 mm between the inductive heating assembly and the surface of the electrically conductive container for most of the surface of the electrically conductive container.

This range of air gap dimensions has been found to provide particularly effective cooling, without significant degradation of the performance of the inductive heating coil.

In an embodiment of the invention, the air channel has a substantially constant cross sectional area for most of the outer surface of the electrically conductive container in a plane perpendicular to a direction in which the air is arranged to flow.

This allows an efficient flow of cooling air.

In an embodiment of the invention, the electrically conductive container is provided with protrusions protruding into the air channel.

This allows improved cooling of the electrically conductive container and so of the test cell.

In an embodiment of the invention, the protrusions are cooling fins. This allows effective cooling.

In an embodiment of the invention, the cooling fins are arranged spirally. This allows an improved cooling effect.

In an embodiment of the invention, the inductive heating assembly is provided with protrusions protruding into the air channel.

This allows an improved cooling effect.

In an embodiment of the invention, the electrically conductive container is located in position with respect to the inductive heating coil by a support member provided with apertures for the passage of air.

This allows effective location of the electrically conductive container while allowing the flow of air.

In an embodiment of the invention, the test apparatus comprises a base member for supporting the base of the electrically conductive container, wherein apertures for the passage of air are provided between the base member and the inductive heating assembly.

This allows effective location of the electrically conductive container while allowing the flow of air.

In an embodiment of the invention the base member is provided with a drain passage for draining fluid from the air channel.

This avoids fluid which may be spilled when filling of the test cell accumulating in the air channel.

In an embodiment of the invention, the upper face of the base member is provided with a retaining wall for directing fluid from the air channel to the drain passage.

This directs fluid spilled into the air channel towards the drain passage and prevents the fluid from being carried in the air stream.

In an embodiment of the invention, the inductive coil is arranged as a plurality of groups of windings and a first axial separation is provided between a first group and a second group of the plurality of groups of windings.

This allows an arrangement of inductive coils which is configured to provide a more uniform heating of the electrically conductive container and the inner electrode by adjustment of the positions of the first and second groups of windings.

In an embodiment of the invention, a second axial separation is provided between the second group and a third group of the plurality of groups of windings, and the second separation is different from the first separation.

This allows an arrangement of inductive coils which is configured to provide a more uniform heating of the electrically conductive container and the inner electrode, by adjustment of the position of the third group of windings.

In an embodiment of the invention, the third group of windings has a minimum radius that is less than a minimum radius of the second group of windings.

This allows a more uniform heating of the electrically conductive container and the inner electrode, in particular for heating sections of the conductive container having a reduced radius, such as a section comprising a drain solenoid.

In an embodiment of the invention, the inductive coil is arranged as a plurality of groups of windings, wherein a first group of windings is contiguous to a second group of windings, and the second group of windings is contiguous to a third group of windings, and wherein the second group of windings has fewer turns per unit length in an axial direction than does the second or third group of windings.

This allows a more uniform heating of the electrically conductive container and the inner electrode.

In an embodiment of the invention, the inductive heating assembly comprises a further inductive heating coil, the further inductive heating coil being separately driven from the inductive heating coil.

This allows the inductive heating coil and the further inductive heating coil to be driven with different electrical signals, so that the fields produced by the respective coils may be adjusted to provide a more uniform heating of the electrically conductive container and the inner electrode.

In an embodiment of the invention, the fluid is insulating oil.

In an embodiment of the invention, the electrical property is resistivity.

In an embodiment of the invention, the electrical property is a dissipation factor measured as a tangent of an angle between capacitive and resistive components of a current flowing through the fluid.

In accordance with a second aspect of the invention, there is provided a method of testing an electrical property of a fluid, comprising:

containing the fluid in an electrically conductive container, the electrically conductive container forming an outer electrode of a test cell;

providing an inner electrode of the test cell arranged to protrude into the electrically conductive container, the inner electrode being electrically isolated from the electrically conductive container;

heating the electrically conductive container and the inner electrode using an inductive heating assembly comprising an inductive heating coil, the inductive heating coil being arranged to surround the electrically conductive container, whereby to heat the test cell to a temperature suitable for testing the fluid;

measuring the electrical property of the fluid using the electrically conductive container as a first electrode and the inner electrode as at least part of a second electrode; and subsequently to heating the test cell, cooling the test cell by causing air to flow through an air channel which is arranged to allow the passage of air across a surface of the electrically conductive container.

This allows the test cell to be cooled by the passage of air across a surface of the electrically conductive container, thereby to reduce the time taken for the test cell to cool sufficiently for safe handling after a test.

In an embodiment of the invention, the method comprises causing air to flow through the air channel at a speed between 1 metre per second and 10 metres per second. This allows effective cooling at an acceptable noise level using a cooling fan assembly. In an embodiment of the invention, the method comprises causing the air to flow through the channel at a speed of substantially 4 metres per second. This has been found to be an effective air speed for effective cooling.

Further features and advantages of the invention will be apparent from the following description of exemplary embodiments of the invention, which are given by way of example only.

DETAILED DESCRIPTION OF CERTAIN INVENTIVE EMBODIMENTS

By way of example, embodiments of the invention will now be described in the context of test apparatus for measuring the resistivity, dielectric dissipation factor, and/or relative permittivity of an insulating oil, in which the dissipation factor may be measured as a tangent of an angle between capacitive and resistive components of a current flowing through the fluid, by applying AC voltage and measuring current, to give a so called "Tan Delta" measurement. For example, electrical properties of a fluid may be measured according to the IEC60247, IEC61620, ASTM D924, ASTM D1169, JIS C2101 and/or BS 5737 standards. It will be understood that embodiments of the invention may relate to test apparatus for measuring electrical properties of other fluids, and that embodiments of the invention are not restricted to measuring resistivity.

Figure 1:
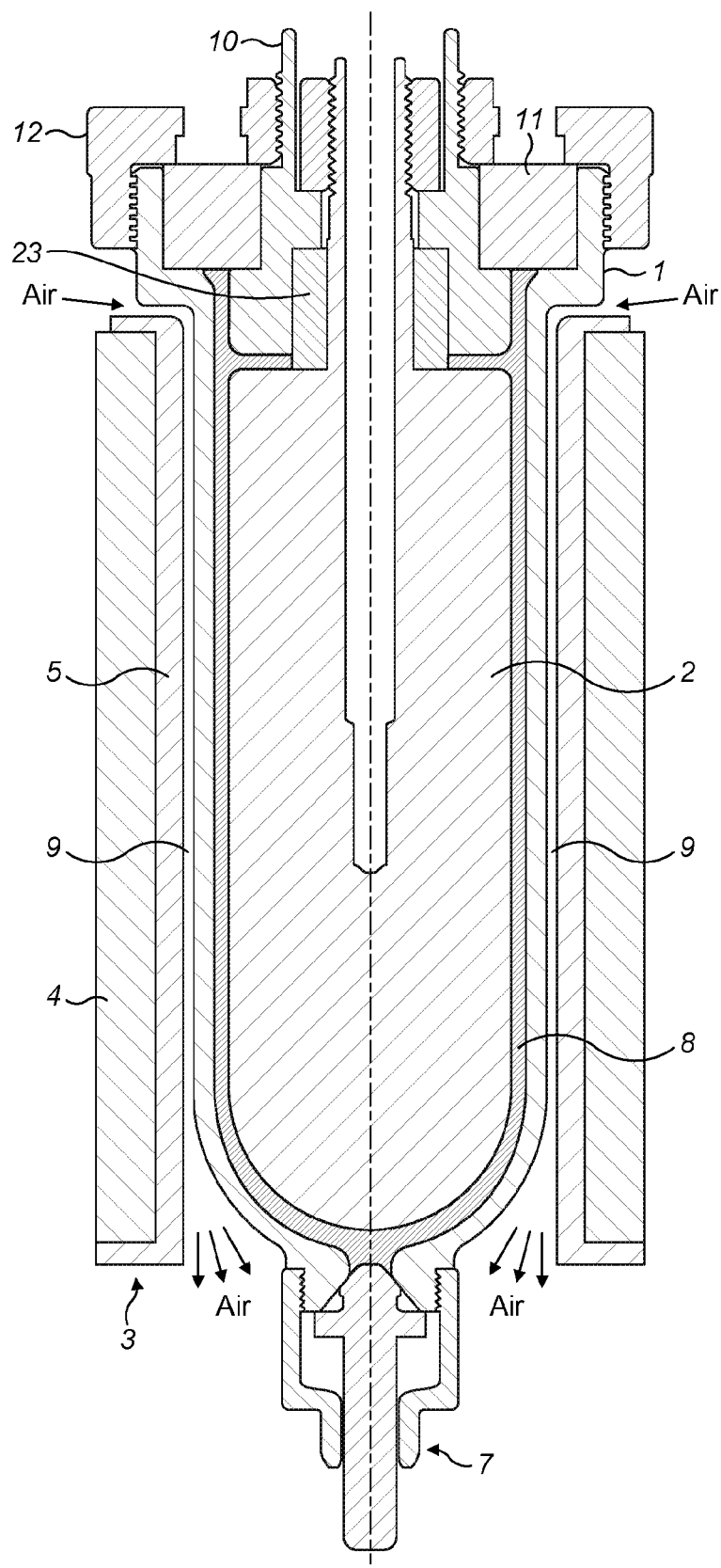
FIG. 1 is a is schematic diagram of a cross-sectional view of apparatus according to an embodiment of the invention.

FIG. 1 is a schematic diagram of test apparatus for testing an electrical property of a fluid according to an embodiment of the invention, in this case a test set for measuring one or more electrical properties including the tan delta factor of an insulating oil for a transformer. The test apparatus comprises an electrically conductive container 1 for containing the fluid, the electrically conductive container 1 forming an outer electrode of a test cell, and comprises an inner electrode 2 of the test cell arranged to protrude into the electrically conductive container 1. FIG. 1 is a cross-sectional view, the test cell being substantially rotationally symmetrical about the dashed centre line. The inner electrode 2 is electrically isolated from the electrically conductive container 1, for example by at least a ring 11, which may be made from glass. A second ring 23, which may also be made of glass, may be used between the inner electrode and the guard, and may touch the oil. The use of two glass rings allows the guard electrode to be accurately positioned with reference to the outer electrode by the first ring 11, and the inner electrode to be accurately positioned with respect to the guard electrode by the second ring 23. In this way, the inner electrode 2 may be mounted and/or located in relation to the electrically conductive container with high precision. The ring 11 may be provided with a hole (not shown) through which an oil under test may be poured to fill the cavity 8 in the test cell between the inner electrode 2 and the conductive container 1. The ring 11 is held in place by top nut 12, which may also act as a thermal insulator.

As shown in FIG. 1, the test apparatus comprises an inductive heating assembly 3 having an inductive heating coil 4 and a coil former 5, for heating the test cell. The coil former is a mechanical support structure for the inductive heating coil. The inductive heating coil may be wound onto the coil former or may be wound elsewhere and then placed onto the coil former. Alternatively the windings may be potted or adhered together, in which case no coil former may be needed. The inductive heating coil 4 is arranged to surround the electrically conductive container 1 and to heat the electrically conductive container 1 and the inner electrode 2, by induction of electrical currents.

As shown in FIG. 1, an air channel 9 is provided to allow passage of air across a surface of the electrically conductive container, for cooling of the electrically conductive container. This allows the test cell to be cooled by the passage of air through the air channel, reducing the time taken for the test cell to cool sufficiently for safe handling after a test. The air channel 9 may be between the inductive heating assembly 3 and the electrically conductive container 1 as shown in FIG. 1 to allow the passage of air across at least part of the outer surface of the electrically conductive container. The air channel may be provided between the coil former 5 and the electrically conductive assembly, so that the air channel and the coil former 5 are between the inductive heating coil 4 and the electrically conductive container 1. The use of the coil former 5 is optional. In an embodiment of the invention, the air channel may be a channel in the electrically conductive container.

As shown in FIG. 1, air may be urged to flow through the air channel, typically from top to bottom as shown. For example, air may be urged to flow due to the creation of a pressure differential from a higher pressure reservoir to a lower pressure reservoir (air reservoirs not shown), from atmospheric pressure to a lower pressure reservoir or from a higher pressure reservoir to atmospheric pressure. Alternatively, air may be urged to flow from bottom to top. The air flow typically cools the conductive container, and so, by conduction, cools the inner electrode. This reduces the time taken for the test cell to cool after a test, and so reduces the waiting time required before the test cell can be handled safely by an operator.

To perform a test of an electrical property of the fluid using test apparatus according to an embodiment of the invention, the electrically conductive container 1 and the inner electrode 2 may be heated using the inductive heating assembly 3 which comprises an inductive heating coil 4, the inductive heating coil 4 being arranged to surround the electrically conductive container 1, to heat the test cell to a temperature suitable for testing the fluid. The electrical property of the fluid may then be measured using the electrically conductive container 1 as a first electrode and the inner electrode 2 as a second electrode, or as at least part of a second electrode. A guard electrode 10 may be used as a further part of the second electrode.

The guard electrode 10 may be provided, to reduce edge effects and improve measurement accuracy. If the guard electrode were not present, then at the top of the test cell there would be a certain capacitance between the outer electrode, which is the electrically conductive container, and inner electrode. The constant separation between the electrodes is typically not maintained at the top of the test cell. Therefore, there may be an edge effect which could have significant influence on the measurement accuracy, due to a capacitive current flowing near the edge which would be difficult to quantify. If a guard electrode is provided, the guard electrode is kept at the same voltage as the inner electrode, so that no current flows between the inner electrode and the guard electrode. A current flowing between the guard electrode and the outer electrode may be shunted away and is not taken into account during the measurement, thus avoiding the edge effect. Because the potential between the inner and the guard is the same, at the transition between the two the field distribution is almost as if the electrode were continuous. Hence capacitance may be measured across a constant thickness of the oil between the electrically conductive container and the inner electrode. A solenoid assembly 7 may be provided so that the fluid may be drained out after a test.

For example, the test of an electrical property of the fluid may be a Tan Delta measurement. Subsequently to heating the test cell for performance of the test, the test cell may be cooled by causing air to flow through the air channel 9 which is arranged to allow the passage of air across a surface of the electrically conductive container 1. This may allow the test cell to be cooled by the passage of air across at least part of the outer surface of the electrically conductive container 1. This reduces the time taken for the test cell to cool sufficiently for safe handling after a test.

Figure 2:
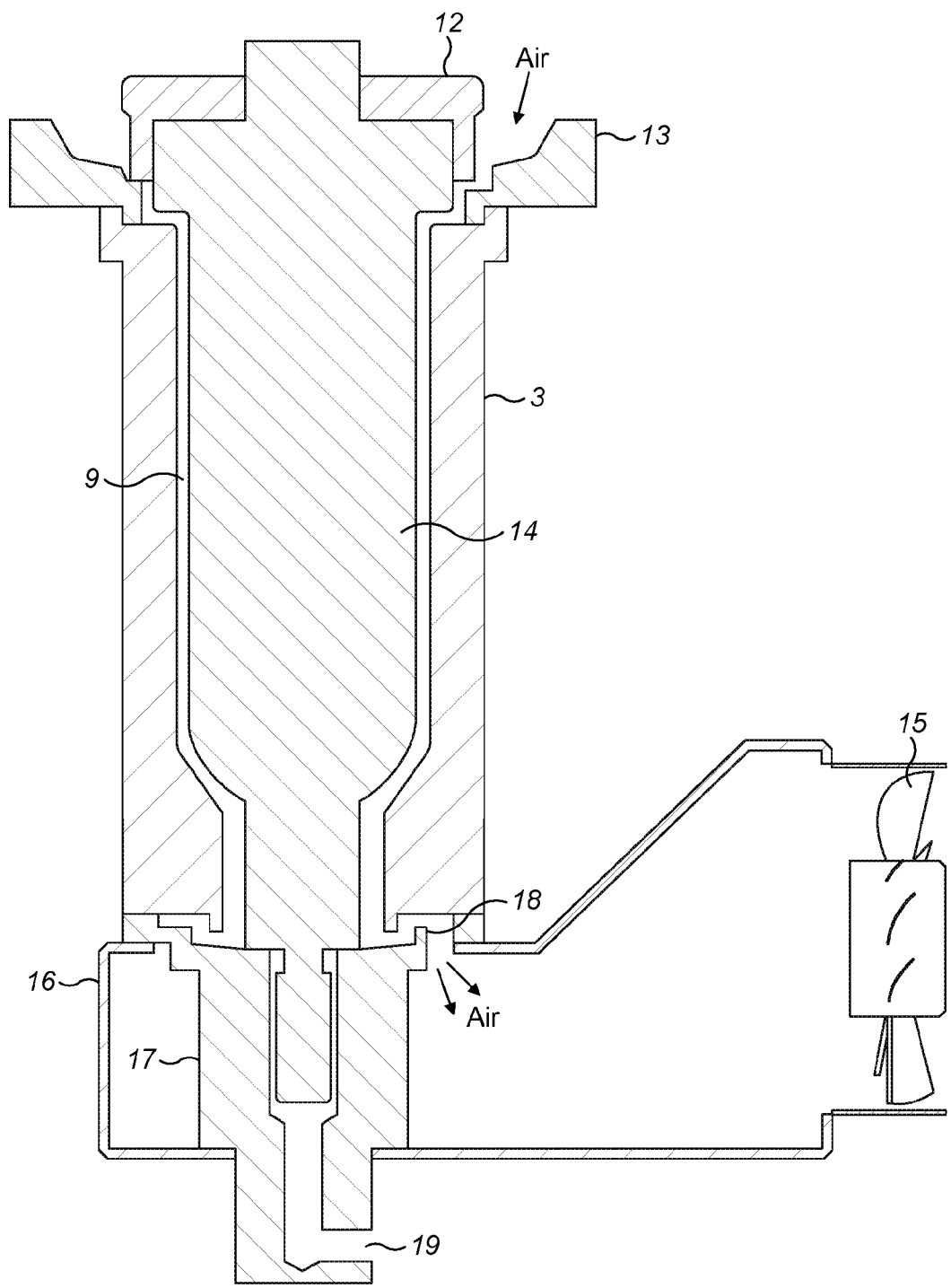
FIG. 2 is a schematic diagram of a cross-sectional view of the apparatus according to an embodiment of the invention comprising a cooling fan.

FIG. 2 is a schematic diagram showing a simplified cross-sectional view of an embodiment of the invention, in which the internal construction of the test cell 14 is not shown. As can be seen, the test apparatus comprises a fan assembly 15 that is arranged to cause air to flow through the air channel 9. In particular, the fan assembly is arranged to extract air from the apparatus and thereby causes a partial vacuum in a vacuum chamber 16, which is attached to the test cell 14 by base member 17, so that air is drawn in from the top of the assembly and through the air channel 9 before being expelled from the apparatus via the fan assembly 15.

The air channel may form part of a "cooling means", which may for example include the air channel, the fan assembly and the vacuum chamber. Alternatively, the cooling means may include the air channel and ducting to connect to an external source of forced air. The air channel allows the passage of air across a surface of the electrically conductive container. The surface may be the outer surface, or at least part of the outer surface of the electrically conductive container. Alternatively or in addition, the surface may be a channel in the wall of the electrically conductive container.

As shown in FIG. 2, the test cell 14 comprises an electrically conductive container and an inner electrode, which has a similar construction to the electrically conductive container 1 and inner electrode 2 shown in FIG. 1. An inductive heating assembly 3 comprises an inductive heating coil and a coil former (not shown), which may, for example, have a similar construction to the inductive heating coil 4 and the coil former 5 shown in FIG. 1. An air channel 9 is provided between the inductive heating assembly and the test cell, typically comprising an air gap between the coil former and the electrically conductive container 1, so that the air channel passes between the inductive coil and the electrically conductive container. It has been found, for this and other embodiments, that an air gap of at least 1 mm between the inductive heating assembly and the electrically conductive container for most of the outer surface of the electrically conductive container may be beneficial in producing a desired cooling effect, and an air gap in the range 2 mm to 4 mm between the inductive heating assembly and the surface of the electrically conductive container for most of the surface of the electrically conductive container defining the air channel, for example for greater than 90% of the surface of the electrically conductive container defining the air channel, has been found to provide particularly effective cooling, without significant degradation of the performance of the inductive heating coil. A larger air gap may also be provided, potentially a gap of 6 mm, 8 mm, 10 mm or greater may be provided.

The air channel may have a substantially constant cross sectional area in a plane perpendicular to a direction in which the air is arranged to flow. Referring to the cross-sectional view in FIG. 2 which is of an embodiment in which the test cell and inductive heating assembly are substantially rotationally symmetrical, it may be seen that the air channel has a larger air gap in cross-section in the section towards the bottom of FIG. 2 in which the radius of the test cell is reduced. In this way, the cross-sectional area, as may be expressed, for example, in square millimetres, may be maintained substantially the same as it is in the section towards the top of FIG. 2 in which the radius of the test cell is greater. Provision of a substantially constant cross-sectional area allows an efficient flow of cooling air, maintaining a substantially constant air speed over the test cell body. An air speed between 1 metre per second and 10 metres per second, and in particular an air speed of 4 metres per second (m/s) has been found to give good cooling performance at an acceptable noise level.

The electrically conductive container may be supported in position with respect to the inductive heating coil by a support member 13 provided with apertures for the passage of air. As shown in FIG. 2, a support member 13 may support the test cell 14, which comprises the electrically conductive container, in position with respect to the inductive heating assembly, 3, by support of the top nut 12. The support 13 may be in direct contact with the nut 12 or with the outer electrode 1, for example. Alternatively or in addition, the cell may be supported from the bottom, in the region adjacent to the solenoid 7. In this case a support may not be required at the top of the test cell to support the weight of the cell, and some form of separator may be provided to hold cell upright and to keep the same gap on each side between the cell and the inductive heating assembly.

Figure 3:
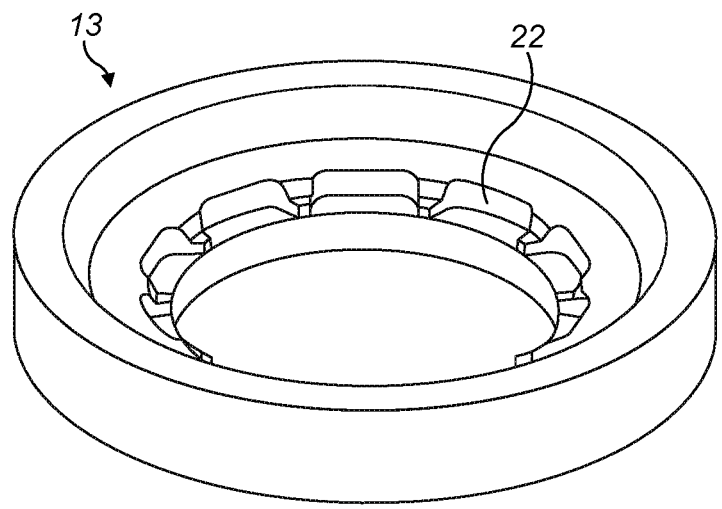
FIG. 3 is a schematic diagram of a perspective view of a support member for locating an electrically conductive container in position with respect to an inductive heating coil, the support member being provided with apertures for the passage of air.

FIG. 3 is a schematic diagram showing a perspective view of support member 13, showing the apertures 22 for the passage of air. In alternative embodiments, there may be more or fewer apertures provided than those shown in FIG. 3.

Returning again to FIG. 2, it can be seen that the test apparatus may comprise a base member 17 for supporting the base of the electrically conductive container, which forms the base of the test cell 14. Apertures for the passage of air from the air channel 9 are provided between the base member 17 and the inductive heating assembly 3, allowing effective support of the electrically conductive container while allowing the flow of air into the vacuum chamber 16. In an embodiment of the invention, there may be no direct contact between the base member 17 and the inductive heating assembly 3. The vacuum chamber 16 may make contact with inductive heating assembly 3. The upper face of the base member 17 is provided with a retaining wall 18 for directing fluid from the air channel to a drain passage, so that any fluid spilled into the air channel is directed towards the drain passage. This may prevent the fluid from being carried in the air stream.

Figure 4:
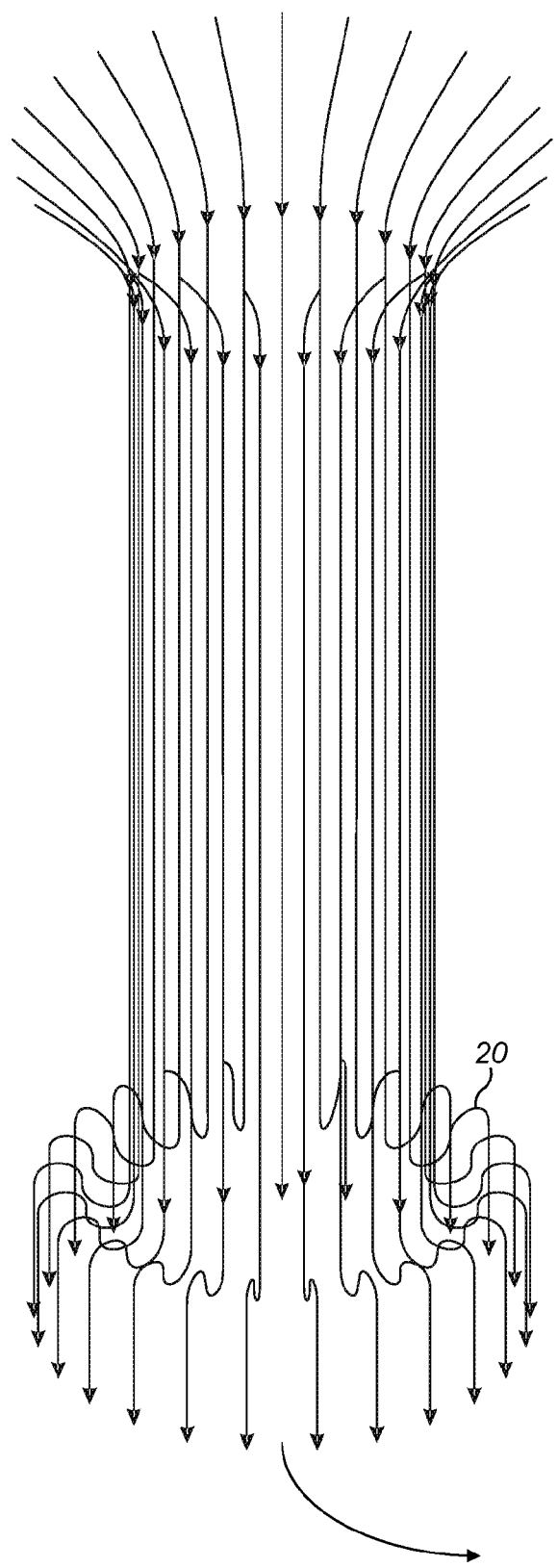
FIG. 4 is a schematic diagram illustrating air flow through an air channel provided in the apparatus in an embodiment of the invention.

FIG. 4 illustrates the direction of the flow of air through the air channel of FIG. 3. Examples are shown of trajectories 20 of the air flow through the air channel.

Figure 5:
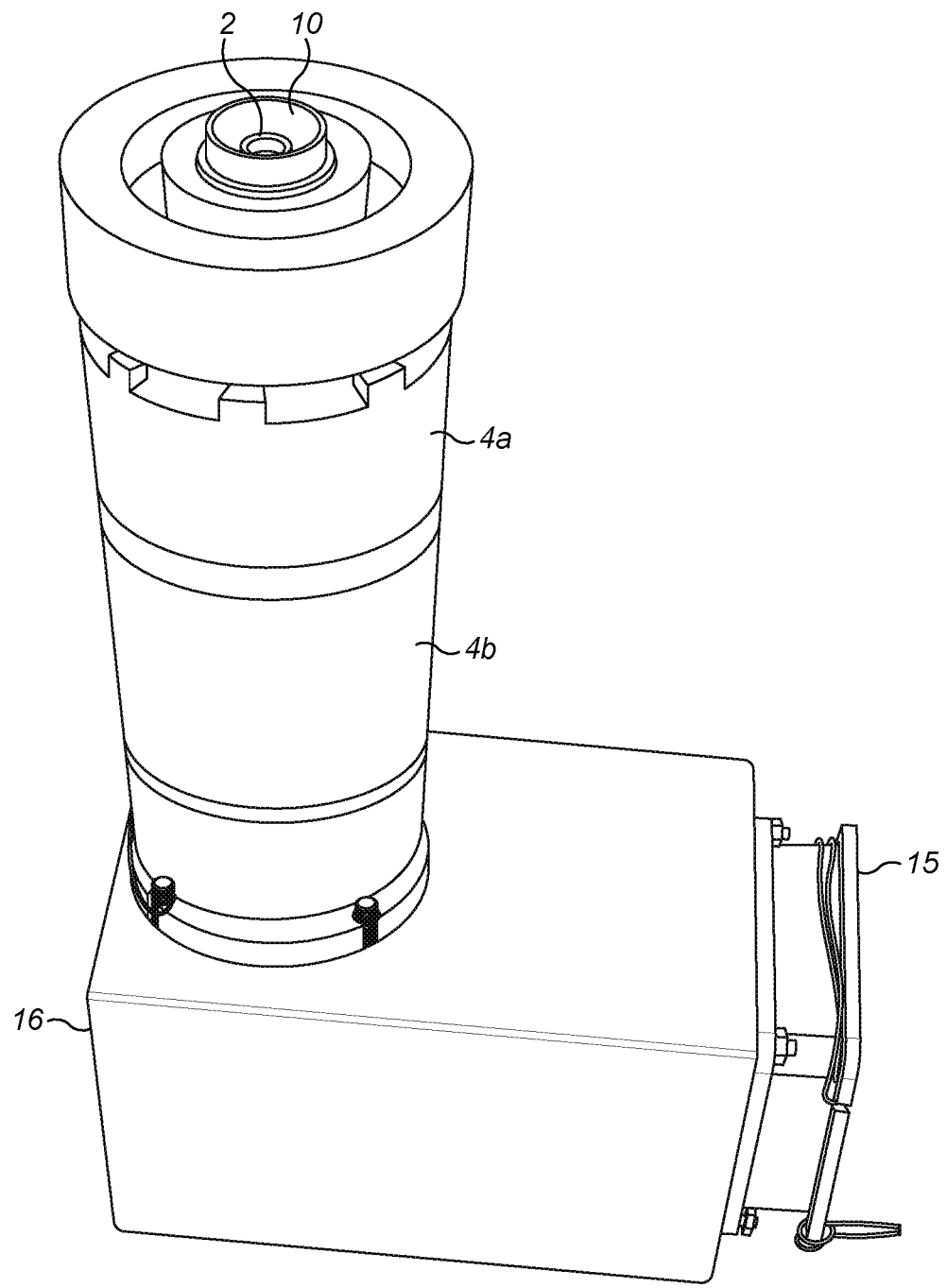
FIG. 5 is schematic diagram of a perspective view of apparatus in an embodiment of the invention.

FIG. 5 shows a perspective view of test apparatus in an embodiment of the invention. The embodiment of FIG. 5, in common with that of FIG. 2, has a fan assembly 15 and vacuum chamber 16, the vacuum chamber having a somewhat different shape as shown in FIG. 5 than that shown in FIG. 2, but having a similar function. In the perspective view of FIG. 5, it can be seen that a top part of the inner electrode 2 and the guard electrode 10 are visible. A support member retains the inductive heating assembly in correct relation to the test cell. As can be seen in FIG. 5, the inductive heating assembly has an inductive coil 4a, 4b arranged as two groups of windings. In this example a first axial separation is provided between the first group 4a and the second group 4b, which provides a more uniform inductive heating of the electrically conductive container and the inner electrode than may be provided by an inductive coil arranged as a single continuous group of windings. If an air channel is provided between the inductive coil and the electrically conductive container, then the non-uniform heating effect may be exacerbated. Arranging the inductive coil as two or more separated groups of windings is expected to mitigate this effect. The positions of the groups of windings may be adjusted to give an improved uniformity of inductive heating effect.

Figure 6:
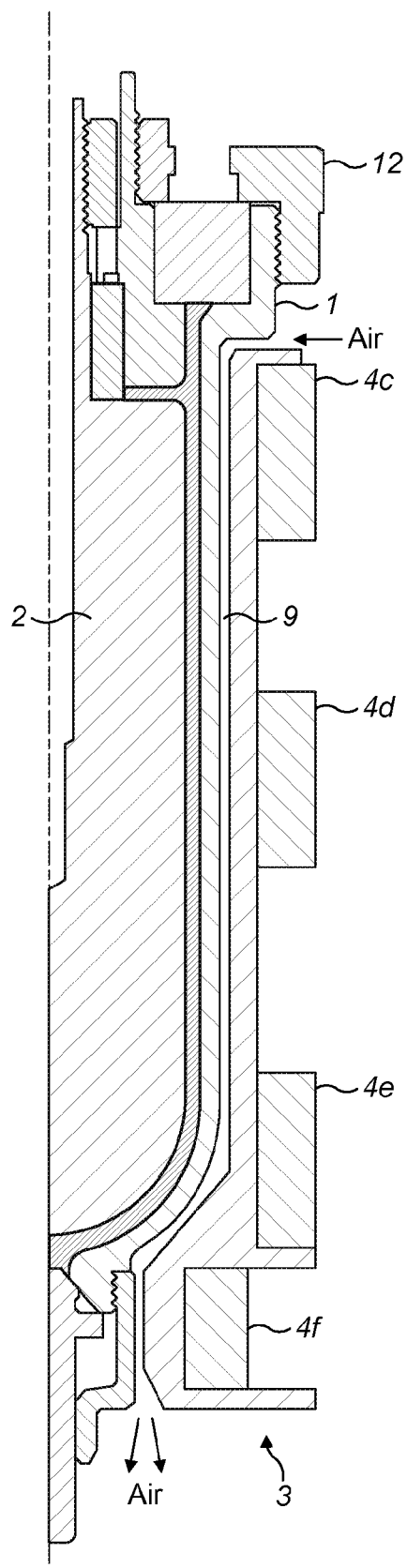
FIG. 6 is schematic diagram of a cross-sectional view of a section of the apparatus in an embodiment of the invention having an inductive heating coil arranged as four groups of windings in which a gap is provided between each group.

FIG. 6 is a schematic diagram showing a cross-sectional view of a section of test apparatus according to an embodiment of the invention, in which the inductive coil 4c, 4d, 4e, 4f is provided as four separated groups of windings. A first axial separation is provided between the first group 4c and the second group 4d, and a second axial separation is provided between the second group 4d and a third group 4e, in which the second separation may be different from the first separation. This use of 3 or more groups of windings is expected to give improved uniformity of heating as compared to the use of only one or two groups. The position of each coil is configured in relation to the test cell to give improved uniformity of heating. Uniformity of heating may be tested, for example, by placing thermocouples into the fluid.

As illustrated by FIG. 6, a fourth group of windings 4f has a minimum radius that is less than a minimum radius of the second group of windings 4d allowing a more uniform heating of the electrically conductive container and the inner electrode, in particular for heating sections of the conductive container having a reduced radius, such as a section comprising a drain solenoid. In the example of FIG. 6, the axial separation between the fourth group of windings 4f and the third group of windings 4e is different from the axial separation between the second group of windings 4d and the third group of windings 4e. Respective groups of windings may be of different thicknesses, that is to say having different numbers of turns per unit length.

In an embodiment of the invention, as an alternative to the arrangement of FIG. 6, the inductive coil may be arranged as groups of contiguous windings of different thicknesses, that is to say having different numbers of turns per unit length. A first group of windings may be contiguous to a second group of windings, and the second group of windings may be contiguous to a third group of windings. The second group of windings may have fewer or more turns per unit length in an axial direction than does the second or third group of windings. This is an alternative method that may allow uniform heating of the electrically conductive container and the inner electrode.

In addition to the inductive heating coil, which may comprise several groups of windings connected together, the inductive heating assembly may comprises a further inductive heating coil that is separately driven from the inductive heating coil. This allows the inductive heating coil and the further inductive heating coil to be driven with different electrical signals, so that the fields produced by the respective coils may be adjusted to provide a more uniform heating of the electrically conductive container and the inner electrode.

Figures 7A, 7B, 7C:
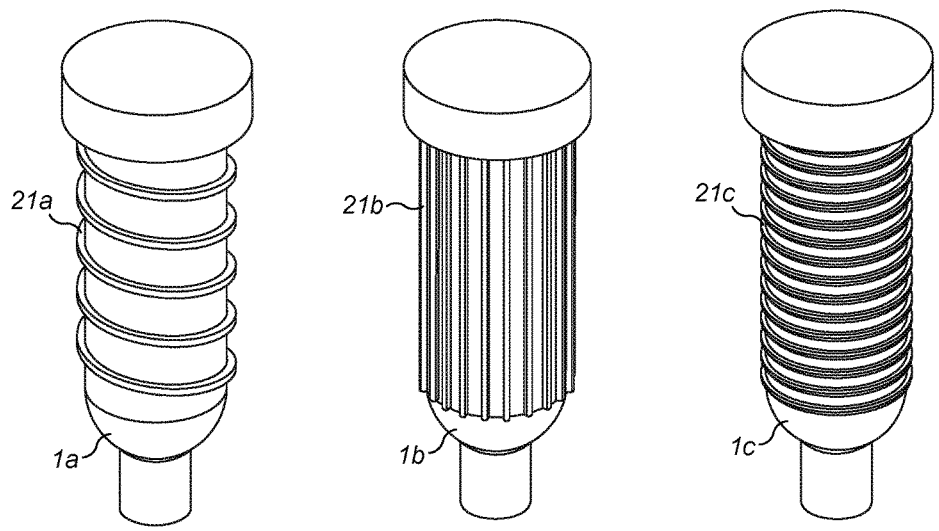
FIG. 7a is a schematic diagram of a perspective view of a conductive container provided with protrusions arranged spirally according to an embodiment of the invention.
FIG. 7b is a schematic diagram of a perspective view of a conductive container provided with protrusions arranged as longitudinal cooling fins according to an embodiment of the invention.
FIG. 7c is a schematic diagram of a perspective view of a conductive container provided with protrusions arranged as circumferential cooling fins according to an embodiment of the invention

As shown in FIGS. 7a, 7b and 7c, the electrically conductive container may be provided with protrusions protruding into the air channel, which may act as cooling fins, allowing improved cooling of the electrically conductive container and so of the test cell. As shown in FIG. 7a, the cooling fins 21a may be arranged spirally, protruding from the electrically conductive container 1a, or, as shown in FIG. 7b, the cooling fins 21b may be arranged longitudinally, protruding from the electrically conductive container 1b, or, as shown in FIG. 7c, the cooling fins 21c may be arranged circumferentially, protruding from the electrically conductive container 1c. In each case, the cooling effect of the passage of air may be improved in comparison with that which may result from the use of an electrically conductive container without protrusions, by increasing the surface area and by altering the air flow, for example to cause turbulent flow.

Alternatively or additionally to providing protrusions on the electrically conductive container, the inductive heating assembly may be provided with protrusions protruding into the air channel. This gives control of air flow, for example to give a turbulent effect.

Embodiments of the invention have been described in the context of specialised measurement and testing equipment for measuring electrical resistivity, tan delta factor, and/or permittivity of transformer oil by applying AC and/or DC voltage and measuring current, from which the electrical property of the oil can be derived. The oil under test is placed in a test cell which comprises several components which perform different tasks. The outer electrode is formed by an electrically conductive container, to which a high voltage, for example up to 2000 V, may be applied. The outer electrode also serves as the container for the oil and as a support for other parts. The outer electrode, which may also be referred to as an outer cell, may be in mechanical contact with the rest of the test instrument. The inner electrode may typically be electrically grounded. Its size may be such that there is a gap of around 2 mm between the inner and the outer electrode. Therefore, it typically has fairly large mass and there may be limited direct thermal connection with the outside world. There may be a hole drilled inside of the inner electrode to insert a thermometer to measure the temperature of the oil, by assuming that during measurement the outer electrode, the oil, and the inner electrode are in thermal equilibrium. The oil under test may fill the gap between the inner and outer electrode, so that the inner-oil-outer system forms an electric capacitor. By applying voltage to this capacitor and measuring current flowing through it the resistivity of oil can be derived. If AC voltage is used then there is a phase shift between capacitive and resistive components of the current. This phase shift can be measured as an angle (delta) and tangent of this angle is proportional to the resistivity, hence the expression "Tan Delta". Induction heating is generated by driving current into the coil, also referred to as the inductive heating coil, for example an AC current of around 2 A at about 1.5 kHz, driven by an AC voltage of about 600V. The coil may be wound on a coil former. In prior art the gap between the outer electrode and the coil former is non-existent or very small, not allowing for the passage of air. This is because in order to improve heating efficiency the coil should be as close as possible to the heated object.

The guard electrode 10, as shown in FIG. 1, may reduce edge effects to improve measurement accuracy. The ring 11 or rings may maintain the concentricity of the inner and outer electrode, which is important for measurement accuracy. The ring or rings may be made with high precision from glass and may determine the positioning between the various parts of the test cell. The oil may be poured from the top and pass through the ring to fill the test cell. A hole may be drilled in the glass, which may be a difficult manufacturing operation, to reduce the size and component count. A solenoid may be provided at the bottom of the cell, so that when activated, it may open a valve and the oil can be drained.

Induction heating is used to induce eddy currents simultaneously in the outer and inner electrodes so that both electrodes warm up in a much more uniform way, and much faster, than could be achieved by heating the outer electrode only. Heating up from room temperature to 90°, which is a typical test temperature, can be achieved in less than 15 minutes. After the test is carried out the test cell might be required to be cooled down. This can be, for example, for removal of the cell for cleaning, or for another test at lower temperature. In embodiments of the invention, air may be blown around the outer electrode to speed up the extraction of heat from the inner cell. This creates a greater thermal difference between the outer and inner electrode and the heat escapes more quickly than under unaided conditions. Simulations and measurements show that the cooling time can be reduced significantly, by a factor of 3 or so, compared to conventional cooling without the passage of air between the outer electrode and the inductive heating coil. For instance, if the safe handling temperature is 50°, to avoid burns to an operator's hands, the "safe handling time" can be reduced from 80 min to 30 min. Using forced air with speed 1.5 m/s or greater has been found to significantly reduce the cooling time, for example in the embodiment of FIG. 2, in which the test cell is mounted on a vacuum box with a fan. The fan extracts the air from the box creating a low pressure. The low pressure sucks the air from the top of the cell through the cylindrical air channel created by the gap.

The induction coil is conventionally designed to be placed closely around the heated object, but in embodiments of the invention, the counterintuitive step has been taken of moving the coil further away from the heated object in order to accommodate the cylindrical air gap for cooling. The heating efficiency has been found to be only slightly worsened by the air gap, so that it is still acceptable. The induction coil used in prior art systems is a single continuous coil. However, the continuous coil used in prior art has a deficiency that the temperature distribution is not uniform along the surface of the oil in the test cell. The effect might be exacerbated by the fact that with the cooling gap the coil is further away from the heated object. Therefore, in order to improve the temperature distribution, a multi-part coil may be used, as illustrated in FIG. 6, whose partial coils, otherwise referred to as groups of windings, are all connected in series for the ease of driving.

A feature which has been found to aid separation of fluid from the cooling air is the "kink" in the air flow 20, as shown in FIG. 4. This is caused by the passage of air over the retaining wall 18 shown in FIG. 2. The direction of the air flow is diverted by more than 90 degrees before returning to substantially the original direction.

The solenoid 7, as shown in FIG. 1, may open a valve which drains oil from the test cell, which rests on the base, otherwise referred to as the base member 17, as shown in FIG. 2, and the mechanical connection may not be completely oil tight. In addition, the oil can be spilled from the top when the cell is being filled through top funnels (not shown). So, provision may be made for oil to flow safely out of the cooling channel. The "kink" in the design will allow for the air to flow, but any oil will drip onto the base and be drained through the valve. Also, in order to improve the air flow around the bottom of the cell the shape of the electrically conductive container is rounded, in contrast to prior art test cells which typically have a flat base. As can be seen from FIG. 2, the cross-section of the cylindrical gap may be maintained at points along the cooling gap. For instance, it can be seen that as the bottom of the test cell 14 cell narrows, the difference between the inner and outer diameters of the gap is increased, so that the effective cross-section area is the same for the air to flow through. The constant area can be achieved also due to the shape of support member 13 in FIG. 2, which mechanically supports the test cell, while providing a passage for air. The support member 13 may be shaped like a crown, as illustrated in FIG. 3, so that the elevated parts support the cell, but between the elevated parts there are channels 22 for the passage of air.

In an alternative embodiment of the invention, openings in the coil former may be provided, to allow for air to be blown across the test cell horizontally, with a fan placed on the side of the cell, rather than vertically as shown for example in FIG. 2.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. Test apparatus for testing an electrical property of a fluid, the apparatus comprising:
    an electrically conductive container for containing the fluid, the electrically conductive container forming an outer electrode of a test cell;
    an inner electrode of the test cell arranged when mounted relative to the electrically conductive container to project into, and remain electrically isolated from, the electrically conductive container;
    an inductive heating assembly comprising an inductive heating coil, which surrounds the electrically conductive container, for heating the electrically conductive container and the inner electrode; and
    cooling means comprising an air channel to allow passage of air across a surface of the electrically conductive container, for cooling of the electrically conductive container.

2. The test apparatus of claim 1, wherein the air channel is provided between the inductive heating assembly and the electrically conductive container.

3. The test apparatus of claim 1, wherein the air channel is provided between the inductive heating coil and the electrically conductive container.

4. The test apparatus of claim 1, wherein the inductive heating assembly and the electrically conductive container are arranged such that the air channel allows the passage of air across at least part of an outer surface of the electrically conductive container.

5. The test apparatus of claim 1, wherein the cooling means comprises a fan assembly that is arranged to cause air to flow through the air channel.

6. The test apparatus of claim 1, wherein the air channel comprises an air gap of at least 1 mm between the inductive heating assembly and the surface of the electrically conductive container.

7. The test apparatus of claim 6, wherein the air gap is in the range of 2 mm to 4 mm.

8. The test apparatus of claim 1, wherein the air channel has a substantially constant cross sectional area.

9. The test apparatus of claim 1, wherein the electrically conductive container is provided with protrusions protruding into the air channel.

10. The test apparatus of claim 9, wherein the protrusions are cooling fins.

11. The test apparatus of claim 10, wherein the cooling fins are arranged spirally around the electrically conductive container.

12. The test apparatus of claim 1, wherein the inductive heating assembly is provided with protrusions protruding into the air channel.

13. The test apparatus of claim 1, wherein the electrically conductive container is mounted in position with respect to the inductive heating coil by a support member that is provided with apertures for the passage of air.

14. The test apparatus of claim 1, comprising a base member for supporting the electrically conductive container, wherein apertures for the passage of air are provided between the base member and the inductive heating assembly.

15. The test apparatus of claim 14, wherein an upper face of the base member is provided with a retaining wall for directing fluid from the air channel to a drain passage.

16. The test apparatus of claim 1, wherein the inductive coil comprises at least a first group of windings and a second group of the windings, wherein a first axial separation is provided between the first group and the second group.

17. The test apparatus of claim 16, wherein the inductive coil further comprises a third group of windings, wherein a second axial separation is provided between the second group and the third group, and wherein the second axial separation is different from the first axial separation, where the third group of windings has a minimum radius that is less than a minimum radius of the second group of windings.

18. The test apparatus of claim 1, wherein the inductive coil is arranged as a plurality of groups of windings, wherein a first group of windings is contiguous to a second group of windings, and the second group of windings is contiguous to a third group of windings, and wherein the second group of windings has fewer turns per unit length in an axial direction than does the first or third group of windings.

19. The test apparatus of claim 1, wherein the inductive heating assembly comprises a further inductive heating coil, the further inductive heating coil being controllable substantially independently of the first-mentioned inductive heating coil.

20. A method of testing an electrical property of a fluid, comprising:

introducing an amount of a fluid to be tested into an electrically conductive container, the electrically conductive container forming an outer electrode of a test cell;

mounting relative to the electrically conductive container an inner electrode of the test cell, to project into, and remain electrically isolated from, the electrically conductive container;

heating the electrically conductive container and the inner electrode using an inductive heating assembly comprising an inductive heating coil, which surrounds the electrically conductive container, whereby to heat the test cell to a temperature suitable for testing the fluid;

measuring the electrical property of the fluid using the electrically conductive container as a first electrode and the inner electrode as at least part of a second electrode; and subsequently to heating the test cell, cooling the test cell by causing air to flow through an air channel which is arranged to allow the passage of air across a surface of the electrically conductive container.

* * * * *